United States Patent
Pongpeerapat et al.

(10) Patent No.: US 8,535,692 B2
(45) Date of Patent: Sep. 17, 2013

(54) LOCAL ANESTHETIC EMULSION COMPOSITIONS AND METHODS OF MAKING AND USING THE SAME

(75) Inventors: Adchara Pongpeerapat, San Jose, CA (US); Toru Hibi, San Jose, CA (US)

(73) Assignee: Teikoku Pharma USA, Inc., San Jose, CA (US)

( * ) Notice: Subject to any disclaimer, the term of this patent is extended or adjusted under 35 U.S.C. 154(b) by 215 days.

(21) Appl. No.: 12/897,531

(22) Filed: Oct. 4, 2010

(65) Prior Publication Data

US 2011/0263715 A1    Oct. 27, 2011

Related U.S. Application Data

(60) Provisional application No. 61/326,613, filed on Apr. 21, 2010.

(51) Int. Cl.
*A61K 47/10* (2006.01)
*A01N 25/00* (2006.01)
*C40B 40/00* (2006.01)

(52) U.S. Cl.
USPC .............................. 424/400; 514/788; 506/13

(58) Field of Classification Search
USPC .................... 424/400; 514/1, 788; 506/7, 13
See application file for complete search history.

(56) References Cited

U.S. PATENT DOCUMENTS

| | | |
|---|---|---|
| 5,601,838 A | 2/1997 | Hind |
| 5,709,869 A | 1/1998 | Hind |
| 5,919,479 A | 7/1999 | Zhang et al. |
| 6,113,921 A | 9/2000 | Friedman et al. |
| 6,245,347 B1 | 6/2001 | Zhang et al. |
| 6,299,902 B1 * | 10/2001 | Jun et al. ........................ 424/449 |
| 6,391,886 B1 * | 5/2002 | Lee ................................ 514/289 |
| 6,528,086 B2 | 3/2003 | Zhang |
| 2002/0006435 A1 * | 1/2002 | Samuels et al. ................ 424/449 |
| 2005/0075407 A1 * | 4/2005 | Tamarkin et al. ................ 521/50 |
| 2006/0088579 A1 * | 4/2006 | Shastri et al. .................. 424/448 |
| 2006/0141031 A1 * | 6/2006 | Nelson et al. .................. 424/464 |
| 2006/0159734 A1 * | 7/2006 | Shudo ............................ 424/448 |
| 2007/0093555 A1 | 4/2007 | Shudo et al. |
| 2008/0253973 A1 * | 10/2008 | Tamarkin et al. ............... 424/47 |

OTHER PUBLICATIONS

Kushla et al., Noninvasive Assessment of Anesthetic Activity of Topical Lidocaine Formulations, J Pharmaceutical Sci, 1993, 82(11), 1118-11122.*

* cited by examiner

*Primary Examiner* — Maria Leavitt
*Assistant Examiner* — Amy M Bunker
(74) *Attorney, Agent, or Firm* — Brian Davy; Bret E. Field; Bozicevic, Field & Francis, LLP

(57) ABSTRACT

Local anesthetic emulsion compositions are provided. The local anesthetic emulsion compositions may include: an oily phase comprising a eutectic mixture of a local anesthetic and an acyclic amide; a surfactant; and an aqueous phase. Also provided are methods of making and using the emulsions.

13 Claims, No Drawings

LOCAL ANESTHETIC EMULSION COMPOSITIONS AND METHODS OF MAKING AND USING THE SAME

CROSS-REFERENCE TO RELATED APPLICATIONS

Pursuant to 35 U.S.C. §119(e), this application claims priority to the filing dates of: U.S. Provisional Patent Application Ser. No. 61/326,613 filed on Apr. 21, 2010; the disclosure of which application is herein incorporated by reference.

INTRODUCTION

The delivery of drugs through the skin provides many advantages. Primarily, such a means of delivery is a comfortable, convenient and noninvasive way of administering drugs. The variable rates of absorption and metabolism encountered in oral treatment are avoided, and other inherent inconveniences, e.g., gastrointestinal irritation and the like, are eliminated as well. Transdermal drug delivery also makes possible a high degree of control over blood concentrations of any particular drug.

Skin is a structurally complex, relatively thick membrane. Molecules moving from the environment into and through intact skin must first penetrate the stratum corneum and any material on its surface. They must then penetrate the viable epidermis, the papillary dermis, and the capillary walls into the blood stream or lymph channels. To be so absorbed, molecules must overcome a different resistance to penetration in each type of tissue. Transport across the skin membrane is thus a complex phenomenon. However, it is the cells of the stratum corneum, which present the primary barrier to absorption of topical compositions or transdermally administered drugs. The stratum corneum is a thin layer of dense, highly keratinized cells approximately 10-15 microns thick over most of the body. It is believed to be the high degree of keratinization within these cells as well as their dense packing which creates in most cases a substantially impermeable barrier to drug penetration. With many drugs, the rate of permeation through the skin is extremely low.

There are many potential uses for topical and transdermal delivery of local anesthetic agents. Such uses include the treatment of burns, contact dermatitis, insect bites, pain, pruritus, skin rash, wounds and other dermal injuries; use as part of or in preparation for a surgical procedure; use as a pretreatment prior to needle injection, such as for subcutaneous injections, venipucture, and in particular for intramuscular or intra joint injections such as for the administration of corticosteroids and other steroids, and so forth.

SUMMARY

Local anesthetic emulsion compositions are provided. The local anesthetic emulsion compositions may include: an oily phase comprising a eutectic mixture of a local anesthetic and an acyclic amide; a surfactant; and an aqueous phase. Also provided are methods of making and using the emulsions.

DETAILED DESCRIPTION

Local anesthetic emulsion compositions are provided. The local anesthetic emulsion compositions may include: an oily phase comprising a eutectic mixture of a local anesthetic and an acyclic amide; a surfactant; and an aqueous phase. Also provided are methods of making and using the emulsions.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Local Anesthetic Emulsion Compositions

Aspects of the invention include local anesthetic emulsion compositions. The local anesthetic emulsion compositions are liquid preparations that are a suspension of small particles (i.e. globules) of one liquid in a second liquid with which the first liquid will not mix. In certain embodiments, the emulsions are emulsions of oil (i.e., the dispersed phase) and water (i.e., the continuous phase).

In some instances, the local anesthetic emulsion compositions include an oily phase comprising a eutectic mixture of a local anesthetic and an acyclic amide; a surfactant; and an aqueous phase. The oily phase is made up of a eutectic mixture of a local anesthetic and an acyclic amide. By eutectic mixture is meant a mixture having a melting point that is less than the melting point of the component parts, i.e., the local anesthetic and the acyclic amide, where these component parts are present in the eutectic mixture as free bases. As such, eutectic mixtures of interest have melting points that are less that the melting point of the local anesthetic of the mixture when the local anesthetic of the mixture is by itself. Likewise, eutectic mixtures of interest have melting points that are less that the melting point of the acyclic amide of the mixture when the acyclic amide of the mixture is by itself. In some instances, the melting point of the eutectic mixture is 27.1° C. or less, such as 24.2° C. or less and including 23.7° C. or less.

The local anesthetic may vary. Local anesthetics of interest are agents that induce local anesthesia by inhibiting nerve excitation or conduction. Local anesthetic agents of interest include, but are not limited to: benzocaine, bupivacaine, butanilicaine, dibucaine, etidocaine, lidocaine, mepivacaine and, prilocalne, tetracaine, and trimecaine, as well as combinations thereof. A given emulsion composition may include a single local anesthetic or two or more different local anesthetic, such that it may include mixtures of two or more local anesthetics. In some embodiments, the local anesthetic is lidocaine. In the emulsion compositions, the amount of local anesthetic may vary. In some instances, the amount of local anesthetic is 20% w/w or greater, such as 30% w/w or greater, and in certain instances ranges from 1 to 20% w/w, such as 1 to 10% w/w.

Also present in the oily phase of the emulsion is an acyclic amide. Acyclic amides of interest include compounds of the formula:

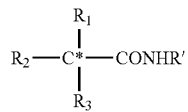

wherein:

$R_1$, $R_2$ and $R_3$ are each $C_1$-$C_5$ alkyl and together provide a total of at least 3, such as from about 3-10, including from about 5-10, carbon atoms; and R' is $C_1$-$C_5$ alkyl, $C_1$-$C_8$ hydroxyalkyl or alkylcarboxyalkyl of up to 8 carbon atoms.

In this group $R_1$ is, in representative embodiments, methyl, ethyl or n-propyl and one or both of $R_2$ and $R_3$ is branched in an alpha or beta position relative to the carbon atom marked (*). As with the local anesthetic, a given emulsion composition may include a single acyclic amide or two or more different acyclic amides, such that it may include mixtures of two or more acyclic amides. In certain embodiments, the cooling agent is N,2,3-trimethyl-w-isopropylbutamide (also known as WS-23; trimethyl isopropyl butanimide, CAS#51115-67-4). In the emulsion compositions, the amount of acyclic amide may vary. In some instances, the amount of acyclic amide is 0.01% or greater, such as 0.05% or greater, and in certain instances ranges from 0.01% to 15% w/w, such as 0.05 to 10% w/w.

The weight ratio of the local anesthetic to the acyclic amide in the eutectic mixture may vary, where in some instances the weight ratio is 5 parts or more local anesthetic to 1 part acyclic amide. In some instances, the ratio is at 6 parts or more, 7 parts or more, 8 parts or more, or 9 parts or more local anesthetic to 1 part acyclic amide.

The total amount of oily phase making up the emulsion compositions may vary. In some instances the total amount of oily phase in the emulsion compositions ranges from 0.01 to 50, such as 10 to 30 and including 15 to 25% w/w.

In addition to the oily phase, the emulsions may include a surfactant. Surfactants of interest include any type of surfactant that can be used for pharmaceutical formulations, including but not limited to, phospholipids, refined phospholipids, nonionic surfactants, or mixtures thereof. Refined phospholipids may include phosphatidylinocytol, phosphatidyl ethanolamine, phosphatidylserine, and sphingomyeline with phosphatidylcholine as a main ingredient. For example, refined phospholipids include egg-yolk lecithin and soybean lecithin. Nonionic surfactants of interest include, but are not limited to, polyethylene glycol, polyoxyalkylene copolymer, and sorbitan fatty acid esters. In some embodiments, the sorbitan fatty acid ester is a polyoxyethylene sorbitan fatty acid ester (e.g., Polyoxyethylene sorbitan tristearate (Tween 65); Polyoxyethylene sorbitan trioleate (Tween 85); Polyethylene glycol 400 monostearate; Polysorbate 60; (Tween 60); Polyoxyethylene monostearate (Myrj 49); Polysorbate 80 (Tween 80); Polysorbate 40 (Tween 40); and Polysorbate 20 (Tween 20)) or sorbitan fatty acid esters (e.g., Sorbitan trioleate (Span 85); Sorbitan tristearate (Span 65); Sorbitan sesquioleate (Arlacel 83); Glyceryl monostearate; Sorbitan monooleate (Span 80); Sorbitan monostearate (Span 60); Sorbitan monopalmitate (Span 40); Sorbitan monolaurate (Span 20)). The amount of surfactant in the emulsion composition may vary. In some instances, the amount of surfactant in the emulsion composition ranges from 0.05 to 5% by weight, such as 0.1 to 1% by weight and including 0.2 to 0.5% by weight. The combination ratio of the oily phase and the surfactant in the emulsion compositions may vary, ranging in some instances from 0.01 to 10, such as 0.05 to 1.

The aqueous phase of the emulsion compositions includes a water. The water present in the emulsions may be any convenient water, including deinionized water, USP water for injection (WFI), etc. The amount of aqueous phase may vary, ranging in some instances from 50 to 95, such as 60 to 80% by weight.

The pH of the emulsion compositions may also vary. In some instances, the pH ranges from 6 to 12, such as 7 to 11 and including 8 to 10.

In some instances, the emulsion compositions may include one or more gelling agents. Gelling agents of interest include, but are not limited to: starch acrylate, polyvinyl alcohol, a carboxyvinyl polymer, hydroxypropyl cellulose, carboxymethyl cellulose, casein sodium, hydroxymethyl cellulose, hydroxyethyl cellulose, hydroxypropylmethyl cellulose, methyl cellulose, polyvinyl pyrrolidone, sodium alginate, a methylvinylether-maleic anhydride copolymer, and the like, and these gelling agents may be used alone or in combination of two or more. A content of the gelling agent in the composition may vary, and in some instances ranges from 1% to 10%, such as 1% to 5%.

Emulsion compositions of the invention exhibit a high local anesthetic flux. By high local anesthetic flux is meant the flux of the local anesthetic agent as measured using the protocol described below is 5 µg/cm²hr or greater, such as 20 µg/cm²hr or greater and including 30 µg/cm²hr or greater, e.g., 40 µg/cm²hr or greater. The local anesthetic flux of the emulsion composition may be determined as follows.

The local anesthetic flux of the emulsion composition may be determined via in vitro skin flux studies using human cadaver epidermal membrane in modified Franz non-jacketed diffusion cells. Merrit & Cooper, 1 J. Controlled Release 161 (1984). In these assays, the epidermal membrane (stratum corneum and epidermis) is separated from whole skin (epidermal membrane and dermis) by the heat-separation method of Kligman & Christopher, 88 Arch. Dermatol. 702 (1963). This method involves the exposure of the full-thickness skin to water at 60° C. for 60 seconds. After this period, the epidermal membrane is gently peeled from the dermis and stored in aluminum foil at −5° C. Prior to skin permeation experiments, the emulsion composition is applied to the stratum corneum side of the thawed epidermal membrane, which is then cut to an appropriate size and placed between the two halves of the diffusion cell with the stratum corneum facing the donor compartment.

The receiver compartment is filled with water or an aqueous buffer appropriate to maintain sink conditions for the drug. All receiver media may include 0.02% (w/w) sodium azide to inhibit bacterial growth. The diffusion cell is placed in a temperature controlled circulating water bath calibrated to maintain the surface temperature of the skin at 32° C. The receiver compartment is constantly stirred by a magnetic stir bar in the receiver compartment agitated by a magnetic stirring module placed under the water bath. At predetermined sampling intervals, the entire contents of the receiver compartment are collected for drug quantitation, and the receiver compartment is filled with fresh receiver solution, taking care to eliminate any air bubbles at the skin/solution interface.

The cumulative amount of drug permeated per unit area at any time t ($Q_t$, µg/cm²) is determined according to the following equation:

$$Q_t = \sum_{t=0}^{t} \frac{C_t V}{A}$$

where $C_t$ (µg/cm³) is the concentration of the receiver compartment at sample time t (hours), V is the volume of the receiver compartment of the diffusion cell and A is the diffusional area of the cell.

Methods of Preparing Emulsion Compositions

Emulsion compositions may be prepared using any convenient protocol. In some instances, emulsion compositions are prepared by combining an amount of the oily phase with the surfactant and aqueous phase in a manner sufficient to produce the desired local anesthetic emulsion composition. The oily phase may be prepared by combining desired amounts of the local anesthetic and the acyclic amide in a manner sufficient to produce the desired eutectic mixture. As such, liquid or solid forms of each component may be combined and, where desired, heated, to produce the desired oily phase. If heat is employed, the components may be heated to above their melting points, e.g., 68-69° C. or above, such as 70° C. or above. Mixing of the components may be achieved using an convenient protocol, including manual and mechanical protocols, where mixing may result in an oily phase that is a homogeneous mixture of the local anesthetic and acyclic amide.

The resultant oily phase is combined with an amount of surfactant and aqueous phase under conditions sufficient to produce the desired emulsion. The emulsion formulation may be prepared according to any convenient protocol. As such, the components of the desired emulsion may be combined with an aqueous medium, e.g., water, under conditions sufficient to produce the desired emulsion. Accordingly, an amount of oily phase and a surfactant may be combined with water under conditions sufficient to produce a emulsion. In the emulsion, the amount of oily phase may range from 0.1 to 500, such as 0.5 to 400 mg/ml. The amount of surfactant (e.g., as described above) may vary, ranging in some instances from 0.5 to 50, such as 1 to 10 mg/ml. The amount of water may range from 0.1 to 100, such as 0.5 to 100%.

The emulsion components may be combined in any convenient order with the aqueous medium. Aqueous media of interest include, but are not limited to: deionized water, USP water for injection (WFI), etc. Certain of the components may be combined with each other, and then combined with the aqueous medium, or all of the components may be combined at substantially the same time. Combination may include various manners of agitation, e.g., stirring, etc., in order to produce the desired precursor emulsion. In certain embodiments, the preparation methods include mixing the oily phase, water and surfactant, and emulsifying the mixture. For example, an aqueous phase, e.g., WFI, can be added to a smooth mixture of an oily phase that includes the surfactant. Initially, the mixture can be roughly emulsified. For example, for rough emulsification, Homomixer (Mizuho Industrial Co., Ltd.) or High Flex Disperser (SMT) can be used. After the mixture is roughly emulsified, the mixture can be finely emulsified, e.g., by using a high pressure emulsification machine. For fine emulsification, a high pressure homogenizer such as Gaulin Homogenizer (APV-SMT) and Microfluidizer (Microfluidics, Newton, Mass.) can be used. In addition, for fine emulsification, the emulsion formulation may be treated by the emulsification machine more than once, such as 2 to 50 times, for example 5 to 20 times, at a pressure ranging from 500 to 850 kg/cm². The preparation methods can be carried out at room temperature or at a temperature lower than room temperature. In certain embodiments, the preparation methods include flushing the emulsification machine with nitrogen gas. Specific examples of protocols for preparing precursor emulsions are provided in the Experimental section, below.

The resultant emulsion composition can be used as is or packaged for a use in a later date, e.g., in a sterile pouch, vial or other suitable container. The container may be a single use or multiple use container. The resultant emulsion composition may also be combined with a suitable delivery device, e.g., carrier. When employed, the delivery device may vary widely. For example, the emulsion may be combined with a cream, lotion or gel delivery vehicle. Alternatively, the emulsion may be combined with a topical patch.

Methods of Use

Methods of using the product local anesthetic emulsion compositions include administering an effective amount of the local anesthetic composition to a subject in order to treat the subject for a target condition of interest. By "treating" or "treatment" is meant at least a suppression or an amelioration of the symptoms associated with the condition afflicting the subject, where suppression and amelioration are used in a broad sense to refer to at least a reduction in the magnitude of a parameter, e.g., symptom, associated with the condition being treated, such as pain. As such, treatment also includes situations where the condition is completely inhibited, e.g., prevented from happening, or stopped, e.g., terminated, such that the subject no longer experiences the condition. As such, treatment includes both preventing and managing a condition.

In practicing the methods, the emulsion compositions disclosed herein can be topically administered to a subject, i.e., the topical compositions may be administered to any convenient topical site. Topical sites of interest include both mucosal and keratinized skin sites, and therefore include, but are not limited to: mouth, nose, eyes, rectum, vaginal, arms, leg, torso, head, etc. The surface area that is covered by the topical composition following application is sufficient to provide for the desired amount of agent administration, and in some embodiments ranges from 1 to 200 $cm^2$, such as from 10 to 180 $cm^2$, and including from 100 to 150 $cm^2$, e.g., 140 $cm^2$.

The topical emulsion composition may be maintained at the topical site to which it has been applied for a desired amount of time, e.g., to deliver a desired amount of local anesthetic to the topical site to which it has been applied. In some instances, the period of time that the composition is maintained at the site of application is 48 hours or less, such as 24 hours or less. The period of time during which the preparation is maintained at the application site is, in some instances, 15 minutes or longer, such as 30 minutes or longer and including 1 hour or longer.

In practicing the subject methods, a given dosage of the topical composition may be applied a single time or a plurality of times over a given time period, e.g., the course of the pain condition being treated, where the dosing schedule when a plurality of compositions are administered over a given time period may be daily, weekly, biweekly, monthly, etc.

In certain embodiments, the topical composition is applied to a keratinized skin site of the subject which may be distal or proximal (depending the particular mechanism of the particular local anesthetic and its effect on the target condition) to the site of pain, where the phrase "site of pain" is used to refer to the location of pain as perceived by subject. The site of pain may be present in a variety of body locations. The skin site (i.e., application site) to which the composition is applied may be sufficiently proximal to the site of pain, e.g. the skin site overlies the region of the site of pain, so that upon contact of the composition with the skin surface, the local anesthetic active agent can act (e.g., by blocking nerve conduction) and exert its desired activity. The particular skin site to which the topical composition may in some instances depend on the location of the site of pain. For example, in treating headache pain, the topical application may be applied to a temple of a subject. Likewise, for treating back pain, the topical composition may be applied to a topical back location of the subject. In certain embodiments, the distance between the site of pain and site of administration does not exceed about 3 cm, and in representative embodiments does not exceed about 1 cm.

The subject compositions are generally applied to the skin site for a period of time sufficient for the desired amount of pain relief to be achieved, where in certain embodiments, the topical composition is applied to the target skin site for a period of time ranging from 0.25 to 24 hours, such as from about 0.5 to 10 hours, including from about 1 to about 8 hours, during which time the subject experiences relief from pain due to the activity of the local anesthetic active agent.

If pain recurs following removal of the topical composition, a new topical composition may be applied. The process may be repeated as necessary and desired to achieve pain relief. In representative embodiments, the patient experiences relief from the pain shortly after application. In certain embodiments, the patient will experience at least some relief from the pain about 0.25 to 30 min following application of the topical composition, usually about 5 to 30 min following application of the topical composition.

In some instances, the amount of composition applied is sufficient to cover a majority of the region of skin overlying the site of pain so that the host experiences pain relief. The exact amount of topical composition that is applied may be determined empirically. For example, the amount of composition applied may be sufficient to cover at least about 50%, more usually at least about 75% of the region. For solutions, dispersions, gels, lotions, creams and the like, the composition may be spread over the region and a covering optionally applied thereto. For patches, an appropriate sized patch may be placed over the region comprising the skin site.

In certain embodiments, the subject methods include a diagnostic step. Individuals may be diagnosed as being in need of the subject methods using any convenient protocol. In addition, individuals may be known to be in need of the subject methods, e.g., they are suffering from pain. Diagnosis or assessment of target condition can be performed using any convenient diagnostic protocol.

Methods of the invention may further include assessing the efficacy of the treatment protocol that includes administration of the local anesthetic emulsion composition. Assessing the efficacy of treatment may be performed using any convenient protocol.

Local anesthetic emulsion compositions of the invention may be administered to a variety of different types of subjects. Subjects of interest include, but are not limited to: mammals, both human and non-human, including the orders carnivore (e.g., dogs and cats), rodentia (e.g., mice, guinea pigs, and rats), lagomorpha (e.g. rabbits) and primates (e.g., humans, chimpanzees, and monkeys). In certain embodiments, the subjects, e.g., patients, are humans.

Utility

The subject emulsion formulations and methods find use in a variety of applications. Applications of interest include the treatment of burns, contact dermatitis, insect bites, pain, pruritus, skin rash, wounds and other dermal injuries; use as part of or in preparation for a surgical procedure; use as a pretreatment prior to needle injection, such as for subcutaneous injections, venipucture, and in particular for intramuscular or intra joint injections such as for the administration of corticosteroids and other steroids, and so forth. Compositions of the invention also find use in the treatment of post-herpetic neuralgia, e.g., as described in U.S. Pat. No. 5,589,180, the disclosure of which is herein incorporated by reference.

Kits

Also provided are kits that find use in practicing the subject methods, as described above. For example, kits for practicing the subject methods may include a quantity of the emulsion composition, present in unit dosages, e.g., vials, or a multi-dosage format. As such, in certain embodiments, the kits may include one or more unit dosages (e.g., vials) of the emulsion composition. The term "unit dosage", as used herein, refers to physically discrete units suitable as unitary dosages for human and animal subjects, each unit containing a predetermined quantity of the subject emulsion composition calculated in an amount sufficient to produce the desired effect. The amount of the unit dosage of the subject emulsion formulation depends on various factors, such as the particular active agent employed, the effect to be achieved, and the pharmacodynamics associated with the active agent in the subject. In yet other embodiments, the kits may include a single multi-dosage amount of the emulsion formulation.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., one or more pieces of paper on which the information is printed, in the packaging of the kit, in a package insert, etc. The instructions may be present on a computer readable medium, e.g., diskette, CD, DVD, etc., on which the information has been recorded. The instructions may be present on a website, which may be used via the internet to access the information at a removed site. Other convenient means are possible and may be included in the kits.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

I. Materials & Methods
A. Test Formulations
1. Ranges of Components

| Lidocaine | 10-20% |
|---|---|
| WS-23 | 0.05-15% |
| Tween 80 | 0.5% |
| Hydroxy Propylcellulose (HPC) | 2% |
| Water qs to | 100% |

2. General Preparation Methods

Formulations above were prepared at up to 20% w/w of lidocaine. The HPC gel was made in water, the required amount of Tween 80 was added to the gel and mixed well in vessel 1. In vessel 2, the required weight of lidocaine and WS-23 were mixed and melted together at 70-75° C. or until the mixture liquefied. The contents of vessel 2 were then added to the contents of vessel 1, slowly and with stirring. Finally, the mixture was mixed with homogenizer for few minutes. The mixture was composed of a eutectic mixture of the pharmacologically active agents (i.e., lidocaine and WS-23) as the internal phase in a gelled emulsion, where solid-crystalline drug was suspended in gelled suspension.

B. Transdermal Flux Tests

Human cadaver skin was used and epidermal layers (stratum corneum and epidermis) were separated from the full-thickness skin as skin membrane. Samples were die-cut with an arch punch to a final diameter of about 2.0 cm². The release liner was removed and the drug delivery system was placed on top of the epidermis/stratum corneum with the drug adhesive layer facing the stratum corneum. Gentle pressure was applied to effect good contact between the adhesive layer and stratum corneum. The donor and receptor sides of the Franz cell were clamped together and the receptor solution containing a phosphate buffer at pH 6.5 was added to the Franz cell. The cells were kept at 33° C. for the duration of the experiment. Samples of the receptor solution were taken at regular intervals and the active agent concentration was measured by HPLC. The removed receptor solution was replaced with fresh solution to maintain the sink conditions. The flux was calculated from the slope of cumulative amounts of the drug in the receiver compartment versus time plot.

II. Results
A. Flux of Lidocaine in Emulsion/Suspension Formulation: WS-23 Loading Effect Using the general method described previously, a series of emulsion/suspension formulations containing different WS-23 loadings in 11.6% lidocaine formulation without gelling agent were prepared with details shown in Table 1. The flux through human cadaver skin were measured and the results are presented in Table 2.

TABLE 1

| Formulation name | % w/w | | | | |
|---|---|---|---|---|---|
| | A | B | C | D | E |
| Lidocaine:WS-23 molar ratio | 9:1 | 8:2 | 7:3 | Lidocaine in Tween | Lidocaine in water |
| lidocaine | 11.6 | 11.6 | 11.6 | 11.6 | 11.6 |
| WS-23 | 0.9 | 2.1 | 3.6 | 0.0 | 0.0 |
| Tween 80 | 0.5 | 0.5 | 0.5 | 0.5 | 0.0 |
| Purified water | 87.0 | 85.8 | 84.3 | 87.9 | 88.4 |
| Total weight | 100.0 | 100.0 | 100.0 | 100.0 | 100.0 |

TABLE 2

| | Formulations | Steady state flux, µg/cm²/hr | SD | Enhancement Ratio |
|---|---|---|---|---|
| A | Eutectic 9:1 | 47.0 | 7.5 | 1.36 |
| B | Eutectic 8:2 | 39.2 | 5.3 | 1.13 |
| C | Eutectic 7:3 | 38.2 | 5.9 | 1.11 |
| D | Lidocaine in Tween | 34.6 | 4.6 | 1.00 |
| E | Lidocaine in water | 36.3 | 6.8 | 1.05 |

B. Flux of Lidocaine in Emulsion/Suspension Formulation: WS-23 Loading Effect

Using the general method described previously, a series of emulsion/suspension formulations containing different WS-23 loadings in 20% lidocaine formulation were prepared with details shown in Table 3. The flux through human cadaver skin were measured and the results are presented in Table 4.

TABLE 3

| Formulation name | % w/w | | | | |
|---|---|---|---|---|---|
| | F | G | H | I | J |
| Lidocaine:WS-23 molar ratio | 9.5:0.5 | 9:1 | 8.5:1.5 | 8:2 | 10:0 |
| lidocaine | 20.0 | 20.0 | 20.0 | 20.0 | 20.0 |
| WS-23 | 0.8 | 1.6 | 2.6 | 3.7 | 0.0 |
| Tween 80 | 0.5 | 0.5 | 0.5 | 0.5 | 0.5 |
| HPC | 2.0 | 2.0 | 2.0 | 2.0 | 2.0 |
| Purified water | 76.7 | 75.9 | 74.9 | 73.8 | 77.5 |
| Total weight | 100.0 | 100.0 | 100.0 | 100.0 | 100.0 |

TABLE 4

| | Formulations | Steady state flux (µg/cm²/hr) | SD | Enhancement Ratio |
|---|---|---|---|---|
| F | 9.5:0.5 Lidocaine:WS-23 | 86.3 | 20.6 | 1.33 |
| G | 9:1 Lidocaine: WS-23 | 74.8 | 16.1 | 1.15 |
| H | 8.5:1.5 Lidocaine:WS-23 | 80.1 | 14.7 | 1.24 |
| I | 8:2 Lidocaine: WS-23 | 75.1 | 17.8 | 1.16 |
| J | Lidocaine only | 64.7 | 13.0 | 1.00 |

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A lidocaine emulsion composition comprising:
   an oily phase comprising a eutectic mixture, the eutectic mixture consisting of lidocaine and N,2,3-trimethyl-w-isopropylbutamide (WS-23);
   a surfactant; and
   an aqueous phase;
   wherein the oily phase, surfactant and aqueous phase are combined.

2. The lidocaine emulsion composition according to claim 1, wherein the surfactant is a phospholipid.

3. The lidocaine emulsion composition according to claim 1, wherein the surfactant is selected from the group consisting of polyethylene glycol, polyoxyalkylene copolymer, sorbitan fatty acid esters, and mixtures thereof.

4. The lidocaine emulsion composition according to claim 3, wherein the surfactant is Polysorbate 80.

5. A lidocaine emulsion composition comprising;
   an oily phase comprising a eutectic mixture, the eutectic mixture consisting of lidocaine and N,2,3-trimethyl-w-isopropylbutamide (WS-23);
   Polysorbate 80; and
   water;
   wherein the oily phase, Polysorbate 80 and water are combined.

6. The lidocaine emulsion composition according to claim 5, wherein the lidocaine emulsion composition exhibits a flux 30 µg/cm² hr.

7. A method comprising applying a lidocaine emulsion composition to a topical location of a subject, wherein the lidocaine emulsion composition comprises:
   an oily phase comprising a eutectic mixture, the eutectic mixture consisting of lidocaine and N,2,3-trimethyl-w-isopropylbutamide (WS-23);
   a surfactant; and
   an aqueous phase;
   wherein the oily phase, surfactant and aqueous phase are combined.

8. The method according to claim 7, wherein the surfactant is a phospholipid.

9. The method according to claim 7, wherein the surfactant is selected from the group consisting of polyethylene glycol, polyoxyalkylene copolymer, sorbitan fatty acid esters, and mixtures thereof.

10. The method according to claim 9, wherein the surfactant is Polysorbate 80.

11. The method according to claim 7, wherein the method is a method of producing anesthesia in a topical location of a subject.

12. The method according to claim 7, wherein the method is a method of treating a subject for post-herpetic neuralgia.

13. A method of producing a lidocaine emulsion composition, the method comprising combining:
   (a) an oily phase comprising a eutectic mixture, the eutectic mixture consisting of lidocaine and N,2,3-trimethyl-w-isopropylbutamide (WS-23);
   (b) a surfactant; and
   (c) an aqueous phase.

* * * * *